United States Patent
Kimura

(10) Patent No.: US 10,220,218 B2
(45) Date of Patent: Mar. 5, 2019

(54) POWER DEVICE FOR IMPLANT MEDICAL DEVICE AND IMPLANT MEDICAL DEVICE

(71) Applicant: PIOLAX, INC., Yokohama-shi (JP)

(72) Inventor: Toshihiro Kimura, Yokohama (JP)

(73) Assignee: PIOLAX, INC., Yokohama-Shi, Kanagawa (JP)

(*) Notice: Subject to any disclaimer, the term of this patent is extended or adjusted under 35 U.S.C. 154(b) by 0 days.

(21) Appl. No.: 15/456,306

(22) Filed: Mar. 10, 2017

(65) Prior Publication Data

US 2017/0266452 A1  Sep. 21, 2017

(30) Foreign Application Priority Data

Mar. 15, 2016 (JP) .................................. 2016-051009

(51) Int. Cl.
| | |
|---|---|
| *A61N 1/378* | (2006.01) |
| *H01F 38/14* | (2006.01) |
| *H02J 7/02* | (2016.01) |
| *H02J 50/10* | (2016.01) |
| *A61N 1/362* | (2006.01) |

(52) U.S. Cl.
CPC ............ *A61N 1/3787* (2013.01); *A61N 1/362* (2013.01); *H01F 38/14* (2013.01); *H02J 7/025* (2013.01); *H02J 50/10* (2016.02)

(58) Field of Classification Search
CPC ......... A61N 1/3787; H02J 50/10; H02J 7/025
See application file for complete search history.

(56) References Cited

U.S. PATENT DOCUMENTS

| | | | | |
|---|---|---|---|---|
| 6,324,431 B1* | 11/2001 | Zarinetchi | ............ | A61N 1/3787 607/33 |
| 6,560,483 B1* | 5/2003 | Kumar | ..................... | A61N 1/30 604/20 |
| 2005/0075696 A1* | 4/2005 | Forsberg | .............. | A61N 1/3787 607/61 |
| 2009/0171404 A1 | 7/2009 | Irani et al. | | |
| 2011/0251687 A1* | 10/2011 | Prescott | ............... | A61N 1/0541 623/10 |

FOREIGN PATENT DOCUMENTS

| | | |
|---|---|---|
| JP | 3743152 B2 | 2/2006 |
| JP | 2009-529975 A | 8/2009 |

* cited by examiner

*Primary Examiner* — William J Levicky
(74) *Attorney, Agent, or Firm* — McGinn I.P. Law Group, PLLC

(57) ABSTRACT

One embodiment provides a power supply device for supplying power to a medical device main body implanted in a human body. The power supply device includes a power supply coil configured to supply power wirelessly to a power reception coil provided in the medical device main body from outside the human body through electromagnetic induction. And, the power supply coil includes: a cylindrical coil formed by winding a lead wire helically; and a ring-shaped member made of a magnetic material and is disposed so as to surround an outer circumference of the cylindrical coil.

15 Claims, 13 Drawing Sheets

POWER DEVICE FOR IMPLANT MEDICAL DEVICE AND IMPLANT MEDICAL DEVICE

CROSS-REFERENCE TO RELATED APPLICATION(S)

This application claims priority from Japanese Patent Application No. 2016-051009 filed on Mar. 15, 2016, the entire contents of which are incorporated herein by reference.

FIELD

The present invention relates to an implant medical device such as a pacemaker and a power supply device for supplying power to an implant medical device.

BACKGROUND

Medical devices may be implanted into human bodies to treat diseases. For example, heart pacemakers are implanted to treat an irregular heartbeat. In general, such pacemakers incorporate a battery for driving a control device and send electric pulses controlled by the control device to the heart muscle via lead wires. However, they need to be replaced before the battery runs down. To replace the battery, the pacemaker need to be removed from the patient body, which is a heavy burden to the patient. In view of this, pacemakers have been developed that incorporate a rechargeable secondary battery that can be charged from outside the human body with the pacemaker kept implanted therein.

For example, JP-3743152-B discloses an electronic device for use in a living body that can be applied to pacemakers etc. This electronic device is equipped with a large gear to which a magnet is fixed, a generator having a small gear which is in mesh with the large gear, a rectification circuit, and a rechargeable secondary battery. A magnetic field generation device having a coil that is connected to an AC power source is set outside a human body. A rotary magnetic field generated by the magnetic field generation device causes rotation of the magnet and hence rotation of the large gear in the electronic device. The small gear is rotated resultantly and causes the generator to generate power, which charges the secondary battery via the rectification circuit.

Whereas the above electronic device for use in a living body incorporates the mechanical power generation structure including the large and small gears, devices are also known that employ a wireless power supply method in which power is supplied from outside a human body through electromagnetic induction. JP-2009-529975-A discloses, as an example device of the latter type, a pacemaker having a wire loop inside and a rechargeable inner battery. A charger for charging the internal battery from outside the human body has a hollow, disc-shaped capsule. Plural rotatable wire loops extend adjacent to the inner wall of the capsule. Referring to FIG. 1 of JP-2009-529975-A, the wire loops in the charger are wound so as to be large enough to be able to be located outside a control device and lead wires provided inside the pacemaker. The charger is brought into contact with a human body surface adjacent to which the pacemaker is implanted and an AC current is caused to flow through the wire loops of the charger. A magnetic flux is generated by the wire loops, whereby a current is induced in the wire loop of the pacemaker and its internal battery is charged.

In the electronic device for use in a living body that is disclosed in JP-3743152-B, if the coil of the magnetic field generation device disposed outside the human body generates an excessively strong magnetic field for the generator of the implanted electronic device to generate sufficient power, a control device, lead wires, etc. of a pacemaker may suffer an adverse effect such as an erroneous operation. Furthermore incorporating the mechanical power generation structure including the large and small gears, the electronic device cannot easily be made compact.

In the pacemaker disclosed in JP-2009-529975-A, since the wire loops of the charger are disposed outside the control device and the lead wires of the pacemaker, a magnetic flux generated by the wire loops of the charger crosses not only the wire loop provided inside the pacemaker but also its control device and lead wires to cause an erroneous operation or the like there.

SUMMARY

One object of the present invention is to provide an implant medical device and a power supply device for an implant medical device in which components, other than a power reception coil, of a medical device main body implanted in a human body is not prone to be affected by a magnetic flux generated by a power supply coil because of concentration of magnetic flux.

An aspect of the present invention provides
a power supply device for supplying power to a medical device main body implanted in a human body, the power supply device including:
a power supply coil configured to supply power wirelessly to a power reception coil provided in the medical device main body from outside the human body through electromagnetic induction,
wherein the power supply coil includes:
a cylindrical coil formed by winding a lead wire helically; and
a ring-shaped member made of a magnetic material and is disposed so as to surround an outer circumference of the cylindrical coil.
There may be provided
the power supply device,
wherein the power supply coil is housed in a cylindrical coil case, and
wherein the coil case is configured to make a marker provided on a human body surface visible through an inside space of the cylindrical coil when an end surface of the coil case in an axial direction thereof is viewed from outside.
There may be provided
the power supply device,
wherein at least one of end walls of the coil case is a transparent member, and/or
wherein the coil case has a penetration space which is defined along an axis of the cylindrical coil.
Another aspect of the present invention provides
an implant medical device including:
a medical device main body to be implanted into a human body; and
a power supply device for supplying power to the medical device main body from outside the human body,
wherein the medical device main body includes:
a power reception coil;
a secondary battery configured to store power generated by the power reception coil; and
a driving device driven by the secondary battery, wherein the power supply device includes:
a power supply coil configured to supply power to the power reception coil wirelessly through electromagnetic induction, and
wherein the power supply coil includes:
a cylindrical coil formed by winding a lead wire helically; and
a ring-shaped member made of a magnetic material and disposed so as to surround an outer circumference of the cylindrical coil.

There may be provided
the implant medical device,
wherein the secondary battery and the driving device are housed in a shield case formed to interrupt magnetism, and
wherein the power reception coil is disposed outside the shield case, and is integrated with the medical device main body with an insulator interposed between the power reception coil and the shield case.

There may be provided
the implant medical device,
wherein the medical device main body includes:
a main body case made of Ti or a Ti alloy and formed to house the shield case, and
wherein the power reception coil is not housed in the shield case but housed in the main body case.

According to the above-mentioned configurations, the power supply coil of the power supply device has the cylindrical coil formed by winding a lead wire helically, and a ring-shaped member which is made of a magnetic material and is disposed so as to surround the outer circumference of the cylindrical coil. This makes it possible to concentrate magnetic flux generated by the power supply coil and to thereby make components, other than the power reception coil, of a medical device implanted in a human body not prone to be affected by the magnetic flux generated by the power supply coil.

DETAILED DESCRIPTION

An implant medical device 10 and a power supply device 50 for an implant medical device according to an embodiment will be hereinafter described with reference to FIGS. 1-11.

Figure 1:
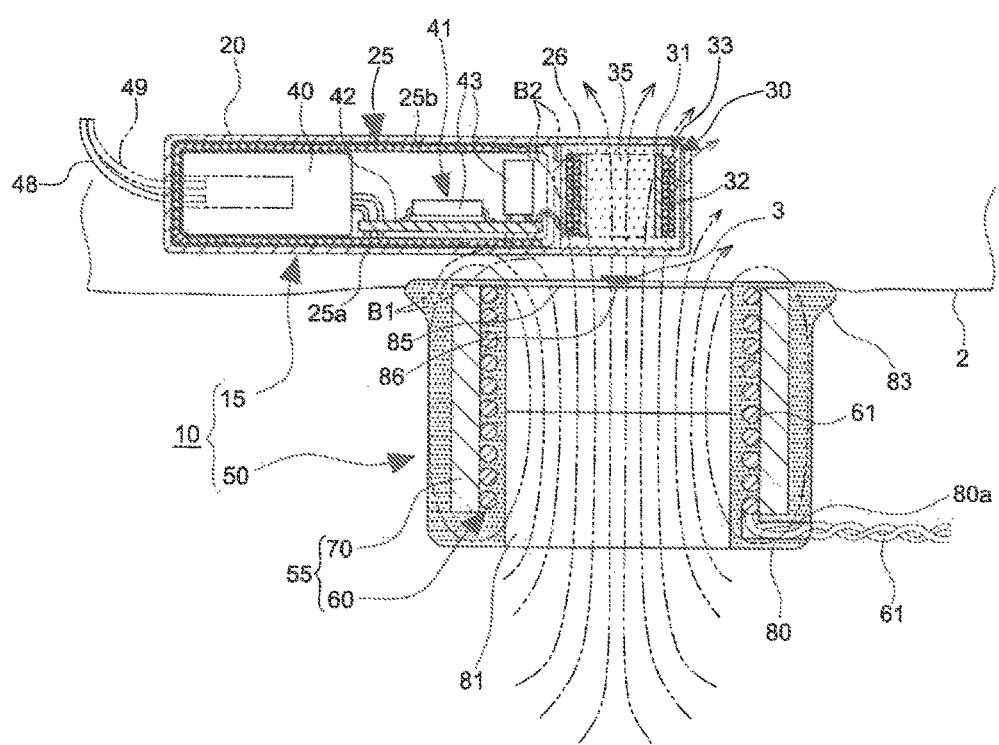
FIG. 1 is a sectional view illustrating an implant medical device and a power supply device for an implant medical device according to an embodiment.
Figure 2:
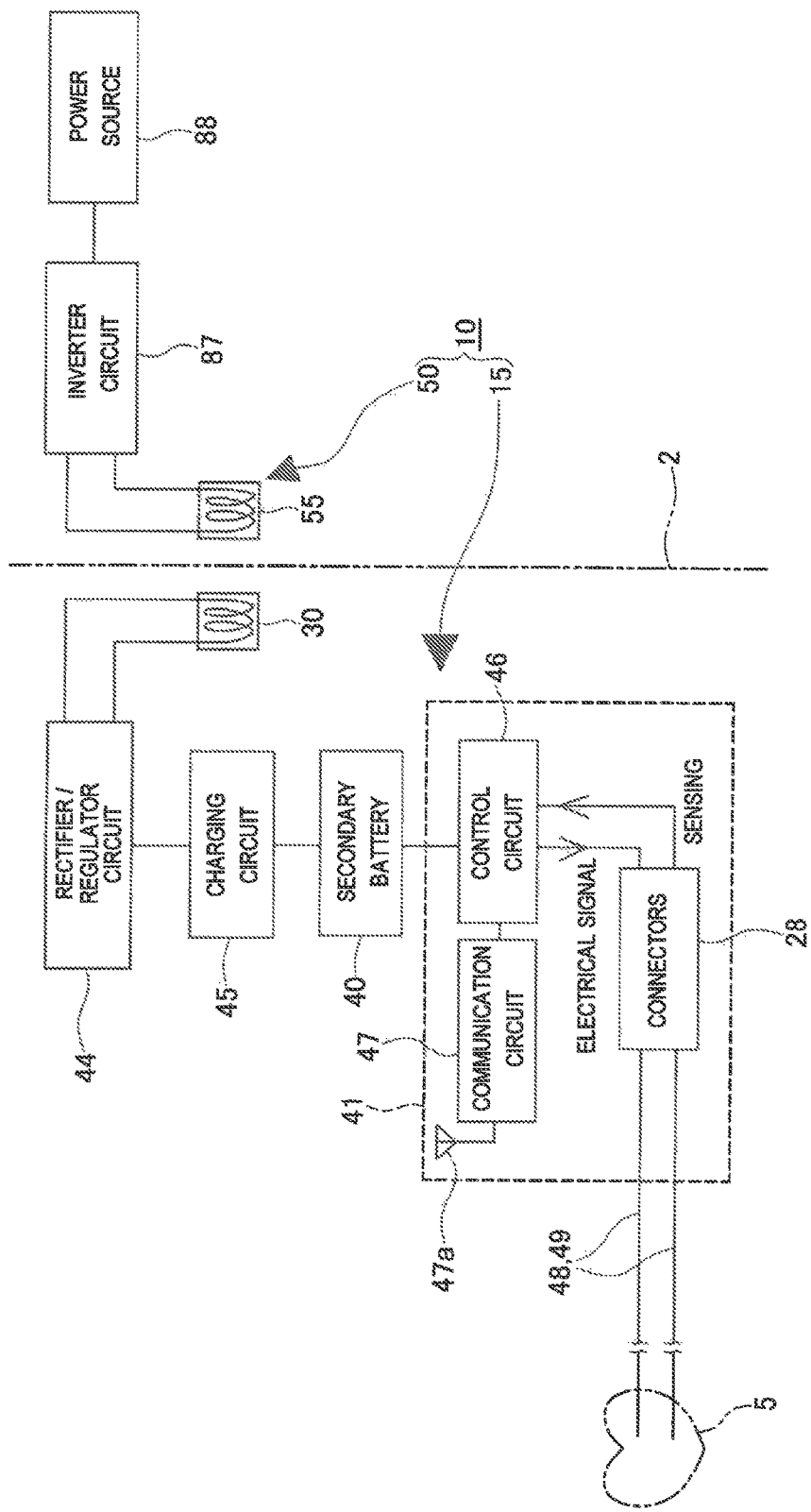
FIG. 2 is a block diagram showing general configurations of the medical device and the power supply device according to the embodiment.

As shown in FIGS. 1 and 2, the implant medical device 10 (hereinafter referred to merely as a "medical device 10") according to the embodiment consists of a medical device main body 15 to be implanted into a human body and the power supply device 50 for supplying power to the medical device main body 15 from outside the human body. In the embodiment, the power supply device 50 is a power supply device of the implant medical device 10.

The medical device 10 according to the embodiment is typically applied to pacemakers to be implanted into human bodies for treatment of cardiac insufficiency etc. However, the medical device 10 can be applied to not only pacemakers but also other artificial organs such as artificial hearts, ventricular assist devices, and artificial kidneys; the medical device 10 can be applied to any implant medical devices.

As shown in FIGS. 1 and 2, the medical device main body 15 (hereinafter referred to as a "device main body 15") is equipped with a power reception coil 30, a secondary battery 40 for storing power generated by the power reception coil 30, and a driving device 41 which is driven by the secondary battery 40.

The medical device main body 15 is equipped with a main body case 20 made of Ti or a Ti alloy and a shield case 25 which is disposed inside the main body case 20 and interrupts magnetism. Also referring to FIG. 3, in the embodiment, the main body case 20 has a flat partition wall 21 and a curved circumferential wall 22 and assumes a box shape.

Figure 3:
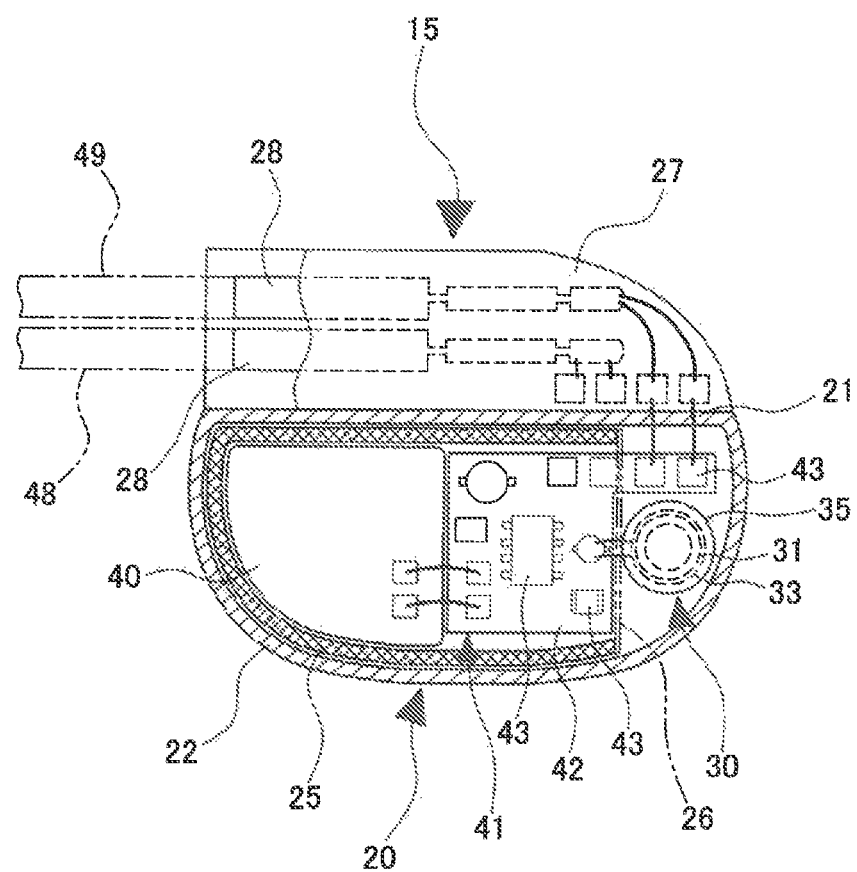
FIG. 3 is a partially sectional view of the medical device according to the embodiment.

As shown in FIGS. 1 and 3, the shield case 25 is shaped like a box that is open on one side and houses the secondary battery 40 and the driving device 41 having a board 42 which is mounted with various circuit components 43.

The shield case 25 may be made of a material having high permeability such as Fe, ferrite, an Fe—Si—B amorphous metal, Mumetal, an Fe—Ni alloy (permalloy), an Fe—Co alloy, silicon steel, ferritic stainless steel, or martensitic stainless steel. Where the shield case 25 is made of a metal material, it is preferable that the metal material be high in conductivity.

Where the shield case 25 is made of a high permeability material, a magnetic flux easily permeates through the shield case 25. Thus, a magnetic flux coming from a power supply coil 55 of the power supply device 50 (described later) and the power reception coil 30 is attracted by and permeates through the shield case 25 (refer to magnetic field lines B1 and B2 in FIG. 1), which makes it possible to suppress influence of magnetism on the secondary battery 40 and the driving device 41. This advantage will be described in detail in a later description of workings and advantages.

To connect end portions of a lead wire 32 of the power reception coil 30 to the board 42 of the driving device 41, one side portion of the shield case 25 is opened. As shown in FIG. 1, the open one side portion of the shield case 25 is set adjacent to the power reception coil 30. As shown in FIGS. 1 and 3, the open one side portion of the shield case 25 may be covered with a shield plate 26 which is made of a material similar to the material of the shield case 25 and is formed with an insertion hole through which end portions of the lead wire 32 of the power reception coil 30 can be inserted. Alternatively, the shield case 25 may be closed on the one side adjacent to the power reception coil 30, too, and formed with a lead wire insertion hole there, with its other side portion opened. As exemplified above, there are no particular limitations on the shape of the shield case 25.

As shown in FIG. 3, a lead connection portion 27 is disposed adjacent to the partition wall 21 of the main body case 20 and connected to the main body case 20. A pair of connectors 28 to which respective lead wires 48 and 49 are connected are arranged parallel with each other inside the lead connection portion 27. The lead connection portion 27 is made of a transparent resin and hence the pair of connectors 28 can be seen from outside.

The above-described shapes and structures of the main body case 20 and the shield case 25 are just examples, and their shapes and structures are not limited to particular ones. For example, the lead connection portion 27 may be integrated with the main body case 20, in which case the connectors 28 are disposed inside the integral structure and the lead wires 48 and 49 are connected to them. For another example, the walls of the main body case 20 may have a multi-layer structure consisting of a Ti layer and a layer of another metal (this structure will be described later in the form of another embodiment.)

Figure 6A:
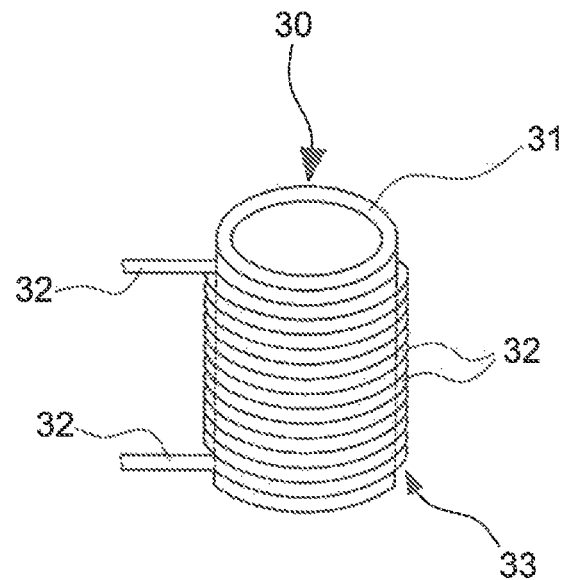
FIG. 6A is a perspective view of a power reception coil, without an insulator, of the medical device according to the embodiment
Figure 6B:
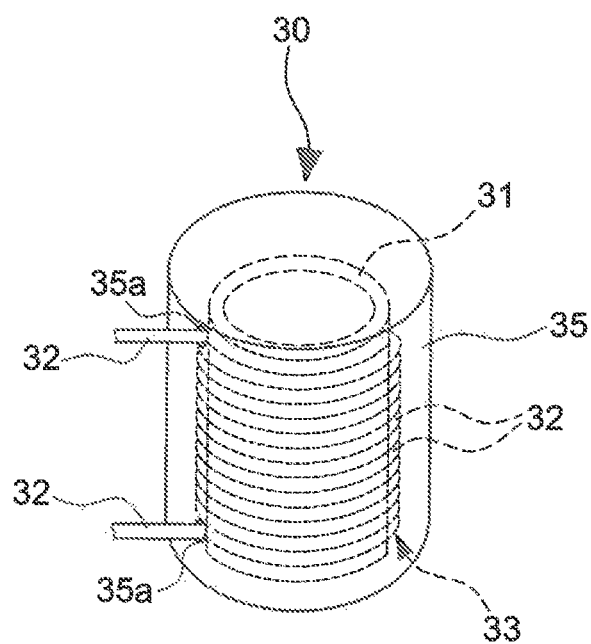
FIG. 6B is a perspective view of the power reception coil with the insulator.
Figure 7A:
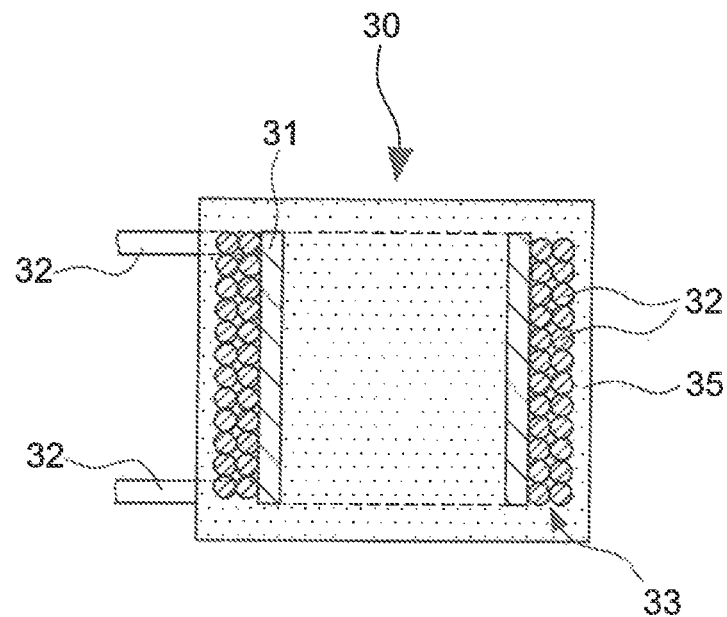
FIGS. 7A and 7B are a sectional view and a plan view of the power reception coil, respectively.
Figure 7B:
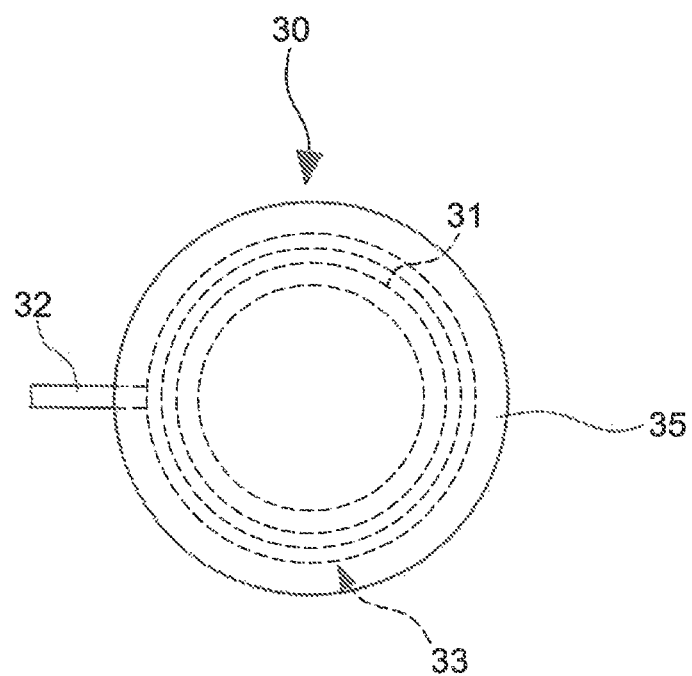
Figure 8A:
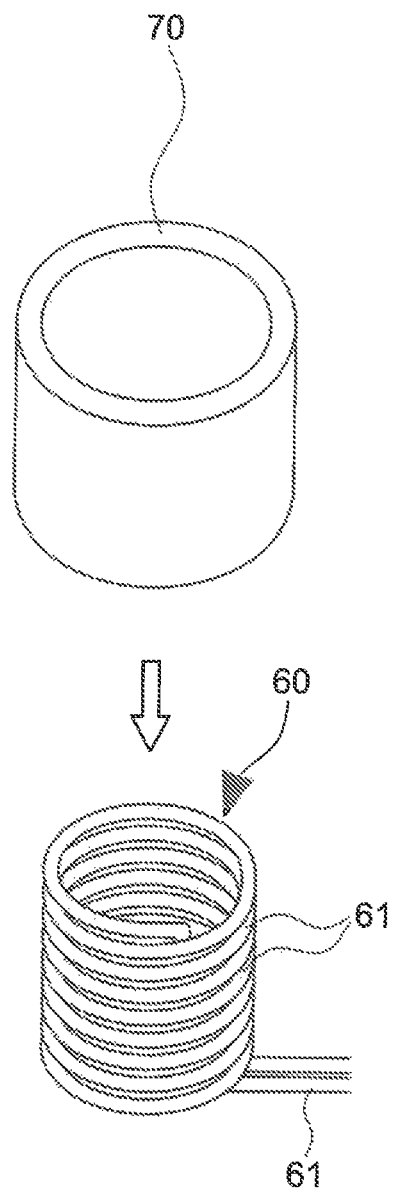
FIGS. 8A and 8B are an exploded perspective view, respectively, of a power supply coil of the implant medical device and the power supply device for an implant medical device according to the embodiment.
Figure 8B:
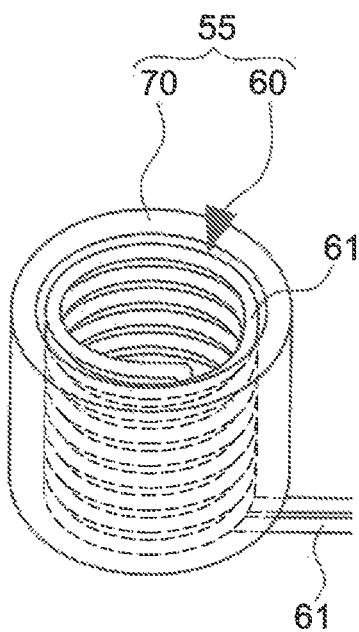

As shown in FIGS. 6A and 6B and FIGS. 7A and 7B, the power reception coil 30 has a cylindrical core body 31 and a cylindrical coil member 33 which is formed by winding a lead wire 32 helically on the outer circumferential surface of the core body 31. The core body 31 and the cylindrical coil member 33 are covered with an insulator 35. As shown in FIG. 7A, the coil member 33 is covered with the insulator 35 from both outside and inside in the radial direction, that is, the whole of the power reception coil 30 is buried in the insulator 35. The insulator 35 has a cylindrical external shape.

As shown in FIGS. 1 and 3, the power reception coil 30 is not housed in the shield case 25 but housed in the main body case 20. And the power reception coil 30 is fixed to the device main body 15 with, for example, a biocompatible adhesive so as to be integral with the device main body 15 such that a part of the insulator 35 is interposed between the coil member 33 and the shield case 25 outside the shield case 25.

Although in the embodiment the power reception coil 30 is integrated with the device main body 15, they may be separated from each other. Although in the embodiment the insulator 35 covers also the inside space of the core body 31 of the power reception coil 30, the inside of the core body 31 may be an empty space. It is preferable that no member that lowers the power reception efficiency of the power reception coil 30 be disposed inside the coil member 33.

As shown in FIG. 6B, a pair of lead-out holes 35a are formed through the insulator 35 at prescribed positions. End portions of the lead wires 32 lead out through the lead-out holes 35a and are connected to a rectifier/regulator circuit 44 (see FIG. 2; described later).

As shown in FIG. 7A, the lead wire 32 is wound closely in plural layers (in this example, two layers). Alternatively, the lead wire 32 may be wound helically with gaps formed between turns or in a single layer or three or more layers. There are no particular limitations on the manner of winding of the lead wire 32.

It is preferable that the diameter of the lead wire 32 be 0.05 to 0.15 mm, and it is even preferable that the diameter of the lead wire 32 be 0.08 to 0.12 mm. It is preferable that the outer diameter of the coil member 33 be 4 to 15 mm, and it is even preferable that the outer diameter of the coil member 33 be 5 to 10 mm. It is preferable that the axial length of the coil member 33 be 1 to 5 mm, and it is even preferable that the axial length of the coil member 33 be 2 to 3 mm.

On the other hand, it is preferable that the outer diameter of the core body 31 be 2 to 13 mm, and it is even preferable that the outer diameter of the core body 31 be 3 to 8 mm. It is preferable that the thickness of the core body 31 be 0.5 to 1.5 mm, and it is even preferable that the thickness of the core body 31 be 0.8 to 1.2 mm. It is preferable that the axial length of the core body 31 be 1 to 5 mm, and it is even preferable that the axial length of the core body 31 be 2 to 3 mm.

Although in the embodiment the core body 31 is shaped like a hollow cylinder, the shape of the core body 31 is not limited to it; the shape of the core body 31 may be a solid cylinder, a hollow prism, a solid prism, or the like. There are no particular limitations on the shape of the core body 31.

The core body 31 may be made of a ferromagnetic material such as ferrite, Fe, iron oxide, chromium oxide, Ni, an amorphous magnetic material, or permalloy. It is preferable to use, among these materials, one whose relative permeability $\mu s$ ($\mu/\mu 0$) is 10 to 500 where $\mu$ is its permeability and $\mu 0$ is the permeability of the vacuum, and even preferable to use one whose relative permeability $\mu s$ is 100 to 200.

It is preferable that the outer diameter and the axial length of the insulator 35 be 5 to 15 mm and 2 to 5 mm, respectively. The insulator 35 may be made of silicone rubber, an epoxy resin, or the like.

As shown in FIGS. 1 and 3, the secondary battery 40 and the driving device 41 having the board 42 which is mounted with the various circuit components 43 such as transistors, integrated circuits, resistors, and capacitors are disposed inside the shield case 25. As shown in FIG. 2, the device main body 15 is equipped with the rectifier/regulator circuit 44 which is connected to the power reception coil 30, a charging circuit 45 which is connected to the rectifier/regulator circuit 44 and the secondary battery 40, a control circuit 46 which is connected to the secondary battery 40, and a communication circuit 47 which is connected to the control circuit 46.

Having both of a rectifier circuit and a regulator circuit, the rectifier/regulator circuit 44 converts an AC current received from the power reception coil 30 into a prescribed DC voltage and supplies the latter to the charging circuit 45. The charging circuit 45 charges the secondary battery 40 using the DC voltage supplied from the rectifier/regulator circuit 44 while controlling it as appropriate.

On the other hand, the control circuit 46 is connected to the secondary battery 40 and is also connected to the lead wires 48 and 49 by the pair of connectors 28. Tip portions of the lead wires 48 and 49 are connected to respective electrodes (not shown), which are connected to an atrium and a ventricle and the heart 5. An electrocardiographic signal of the atrium and the ventricle of the heart 5 is input to the control circuit 46 via the lead wires 48 and 49 and the connectors 28 (sensing). The control circuit 46 judges, on the basis of the electrocardiographic data, whether or not the heart 5 is producing an irregular heartbeat or the like. If finding an irregular heartbeat or the like, the control circuit 46 sends an electrical signal to the lead wires 48 and 49 via the connectors 28. Thus, the atrium and the ventricle of the heart 5 are stimulated electrically (pacing).

The communication circuit 47 which is connected to the control circuit 46 is also connected to an antenna 47a. The communication circuit 47 sends electrocardiographic data, sensing data, pacing data, charging information of the secondary battery 40, etc. that are received from the control circuit 46 to an external apparatus such as an external monitor via the antenna 47a. The communication circuit 47 receives control signals for the control circuit 46, the secondary battery 40, etc. via the antenna 47a.

Among the above-described components, functions of the control circuit 46 and the communication circuit 47 shown in FIG. 2 are physically realized by the components of the driving device 10 shown in FIG. 3 etc. Meanwhile, in the present invention, the term "driving device" may conceptually include not only the control circuit 46 and the communication circuit 47 but also, for example, the lead wires 48 and 49. The medical device 10 according to the embodiment requires the lead wires 48 and 49 for transmitting an electrical signal to the heart because it is also used as a pacemaker. However, where the medical device 10 is used in another artificial organ, a medical tube, a pump, a motor that is driven by the pump, a filter, a sensor, etc., for example, may be employed as components of the driving device.

The lead wires 48 and 49 are not disposed in the shield case 25, and their base portions are connected to the connectors 28 which are provided in the lead connection portion 27 of the device main body 15. The expression "the driving device is housed in a shield case" as used in the claims means not only a mode that the entire driving device is housed in the shield case but also a mode that only part of the driving device is housed in the shield case.

Although it has been mentioned that the device main body 15 is equipped with the rectifier/regulator circuit 44, the charging circuit 45, the control circuit 46, the communication circuit 47, etc., these circuits are just examples; it goes without saying that the device main body 15 may be equipped with other circuits.

Figure 4:
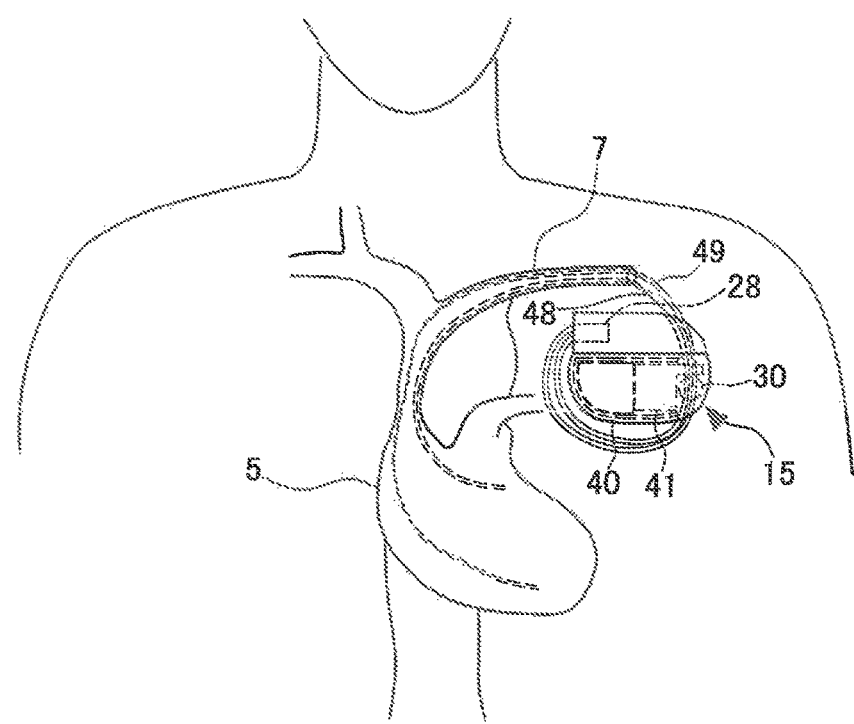
FIG. 4 is an explanatory front view of a human body illustrating an example method for using the medical device according to the embodiment.

As shown in FIG. 4, when the device main body 15 as implanted in a human body is viewed from the front side of the human body, portions, extending from the connectors 28, of the lead wires 48 and 49 which are connected to the device main body 15 via the connectors 28 are bent so as to go around the outer circumference of the device main body 15, pass the device main body 15, are then inserted into a vein 7, and are finally connected to the atrium and the ventricle of the heart 5. Thus, although the lead wires 48 and 49 appear to be close to the power reception coil 30 when the device main body 15 is viewed from the front side of the human body (see FIG. 4), in actuality they are not close to the power reception coil 30.

Figure 5:
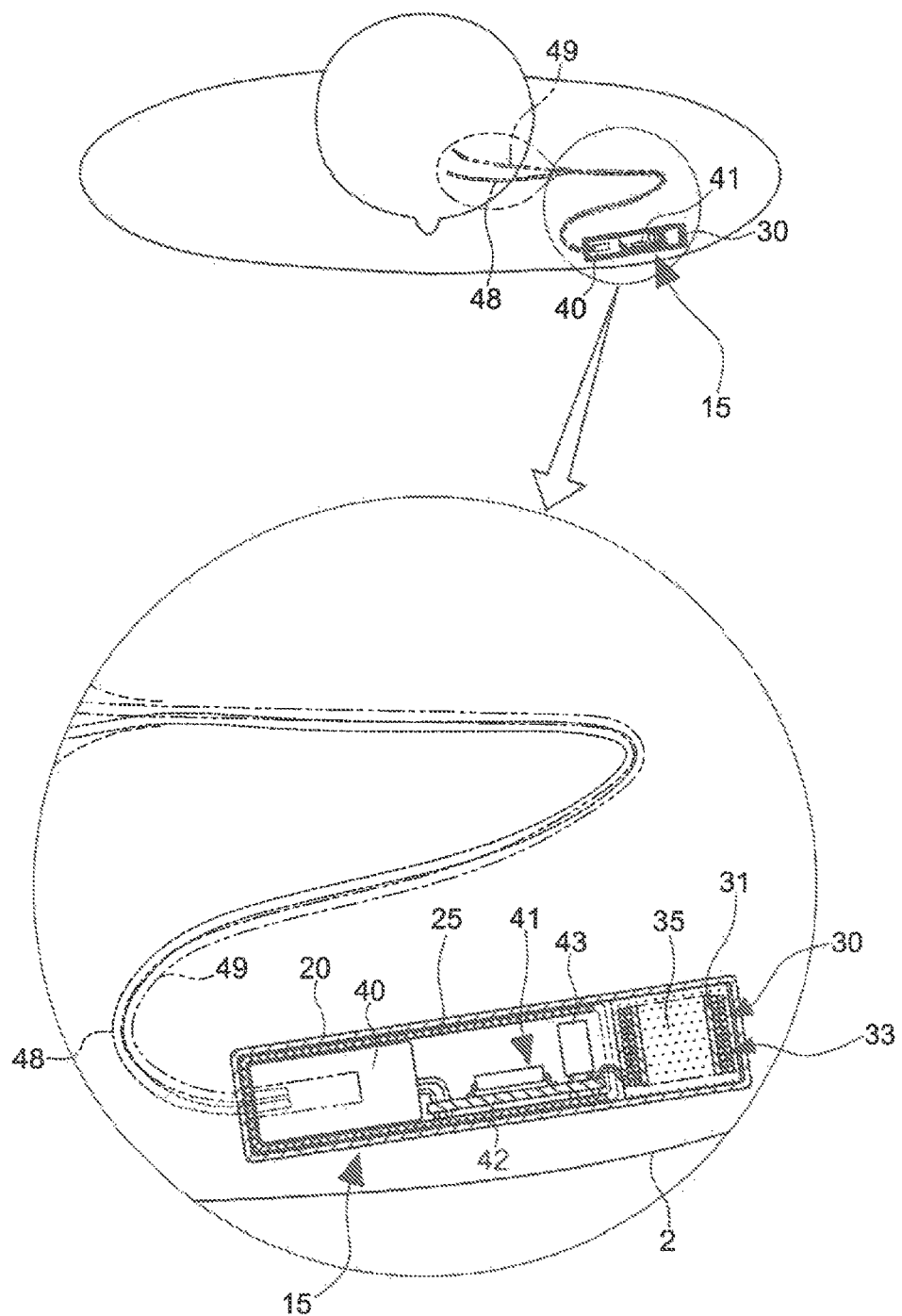
FIG. 5 is a plan view (i.e., a view as viewed from above the head) illustrating the example method for using the medical device according to the embodiment.

More specifically, as shown in FIG. 5, in a plan view, that is, when the human body is viewed from above the head, the lead wires 48 and 49 gradually goes away from the device main body 15 on the back side of the device main body 15 while being curved so as to form a gentle mountain shape and is then inserted into the vein 7. The lead wires 48 and 49 are therefore distant from the power reception coil 30 and hence are not affected by a magnetic field generated by the power supply coil 55 of the power supply device 50 or the power reception coil 30.

Incidentally, in general, battery-replacement-type pacemakers employ an all-solid-state primary battery such as a lithium iodide battery. However, in the embodiment, it is preferable that the secondary battery 40 employ an all-solid-state secondary battery that uses, as a solid-state electrolyte, lithium phosphate, glass ceramic (Li7P3S11), or the like. It is said that all-solid-state secondary batteries are much larger in the battery capacity per unit area, than all-solid-state primary batteries. Even if it is assumed that an all-solid-state secondary battery that should be charged once each year is the same in performance as an all-solid-state primary battery that is usable for 10 years, the size of the former can be made 1/10 of that of the latter. If the all-solid-state secondary battery is two times as good in performance as the all-solid-state primary battery, the size of the former can be made 1/20 of that of the latter.

It is preferable that the voltage of the secondary battery 40 be 3.0 to 3.5 V and its capacity be larger than or equal to 120 mA·h.

Next, a description will be made of the power supply device 50 for an implant medical device according to the embodiment. As shown in FIG. 1, the power supply device 50 according to the embodiment is equipped with a power supply coil 55 for supplying power wirelessly (i.e., through electromagnetic induction) from outside a human body to the power reception coil 30 provided in the device main body 15.

As shown in FIGS. 8A and 8B to FIG. 10, the power supply coil 55 is composed of a cylindrical coil 60 formed by winding a lead wire 61 helically and a ring-shaped member 70 which is made of a magnetic material and disposed so as to surround the outer circumference of the cylindrical coil 60.

Although in the embodiment the cylindrical coil 60 is formed by winding the lead wire 61 helically with gaps formed between turns, it may be wound closely. It is preferable that the diameter of the lead wire 61 be 0.1 to 1.0 mm, and it is even preferable that the diameter of the lead wire 61 be 0.2 to 0.5 mm. It is preferable that the outer diameter of the coil member 60 be 10 to 50 mm, and it is even preferable that the outer diameter of the coil member 60 be 20 to 30 mm. It is preferable that the axial length of the coil member 60 be 10 to 50 mm, and it is even preferable that the axial length of the coil member 60 be 20 to 30 mm. It is preferable that the gap between adjoining turns of the lead wire 61 be 0.05-0.5 mm, and it is even preferable that the gap between adjoining turns be 0.1 to 0.2 mm.

Although in the embodiment the ring-shaped member 70 is shaped like a circular ring having a prescribed axial length, the ring-shaped member 70 may be shaped like a square ring. It suffices that the ring-shaped member 70 be able to surround the entire outer circumference of the cylindrical coil 60.

By disposing the ring-shaped member 70 made of a magnetic material outside the cylindrical coil 60, the width W of the magnetic-flux-concentrated range can be made smaller (see FIG. 11A) than in a case that the ring-shaped member 70 is not provided (see FIG. 11B), even though the magnetic flux produced by the power supply coil 55 remains approximately the same. This advantage will be described in detail in a later description of workings and advantages.

Figures 9A, 9B:
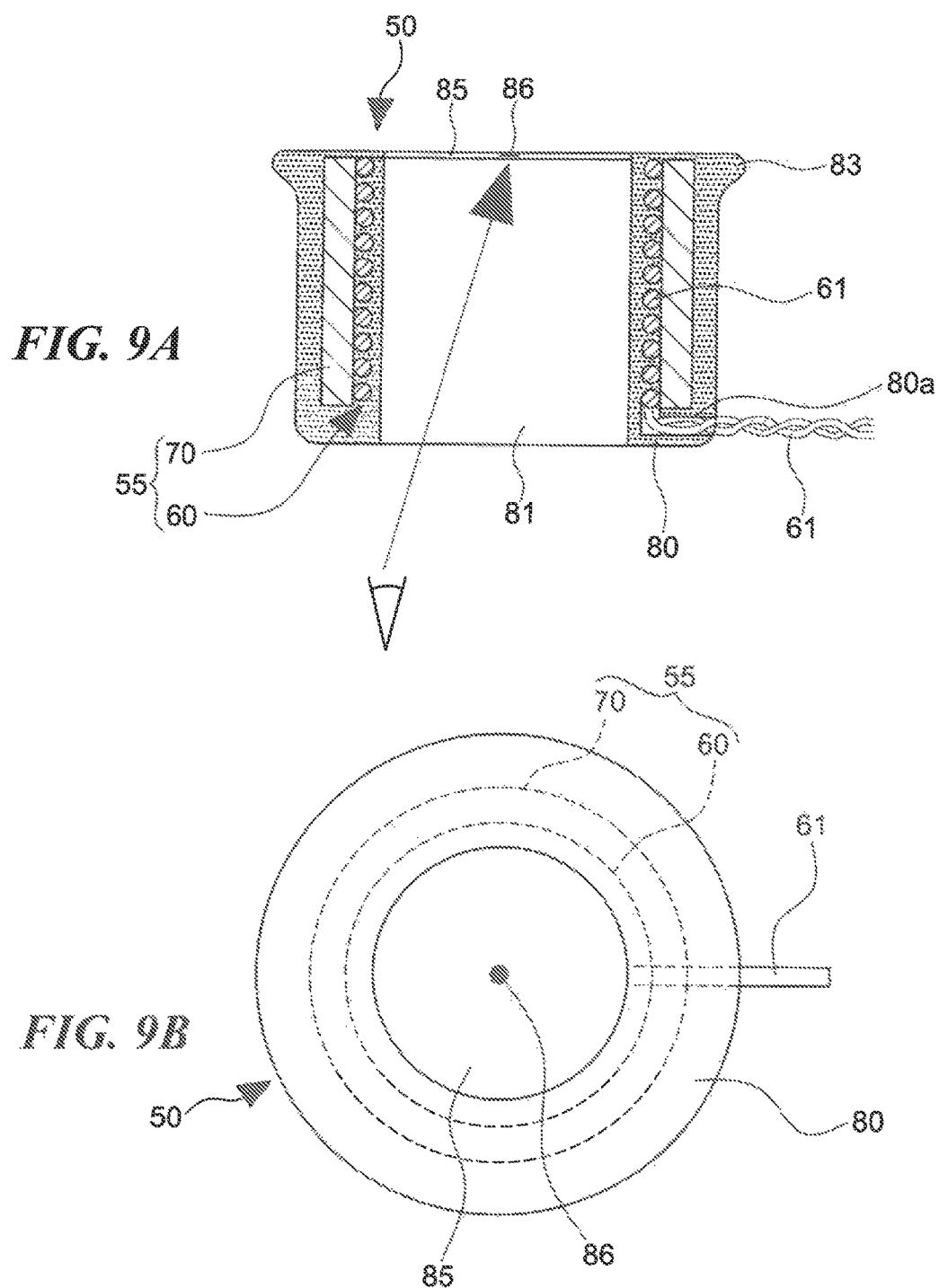
FIGS. 9A and 9B are a sectional view and a plan view of the power supply coil, respectively.

In the embodiment, as shown in FIG. 9A, the ring-shaped member 70 is disposed outside the cylindrical coil 60 such that their tips in the axial direction are located approximately at the same position. However, the ring-shaped member 70 may stick out of the tip of the cylindrical coil 60. There no particular limitations on the positional relationship between the tips of the ring-shaped member 70 and the cylindrical coil 60.

In the embodiment, as shown in FIG. 9A, two end portions the lead wire 61 of the cylindrical coil 60 which is disposed inside the ring-shaped member 70 lead out of the base side of the ring-shaped member 70 so as to extend outward in the radial direction, that is, perpendicularly to the axis of the ring-shaped member 70. Alternatively, two end portions the lead wire 61 of the cylindrical coil 60 may lead out of the ring-shaped member 70 so as to extend parallel with the axis of the ring-shaped member 70. There no particular limitations on the manner in which two end portions the lead wire 61 lead out of the ring-shaped member 70.

It is preferable that the outer diameter of the ring-shaped member 70 be 20 to 60 mm, and it is even preferable that the outer diameter of the ring-shaped member 70 be 25 to 35 mm. It is preferable that the thickness of the ring-shaped member 70 be 0.5 to 10 mm, and it is even preferable that the thickness of the ring-shaped member 70 be 1 to 5 mm. It is preferable that the axial length of the ring-shaped member 70 be 10 to 50 mm, and it is even preferable that the axial length of the ring-shaped member 70 be 20 to 30 mm; it is preferable that the ring-shaped member 70 be long enough to cover the cylindrical coil 60 over its full length. Although in the embodiment the ring-shaped member 70 is approximately the same in length as the cylindrical coil 60 and hence can cover the cylindrical coil 60 fully (see FIG. 9A), the ring-shaped member 70 may be either longer or shorter than the cylindrical coil 60.

Although in the embodiment the inner diameter of the ring-shaped member 70 is set so that its inner circumferential surface comes into contact with the outer circumference of the cylindrical coil 60, a prescribed gap may be formed between the inner circumferential surface of the ring-shaped member 70 and the outer circumference of the cylindrical coil 60. It is preferable that the gap be 0.5 to 3 mm, and it is even preferable that the gap be 1 to 2 mm.

The ring-shaped member 70 is made of a magnetic material, and may be made of a ferromagnetic material such as Fe, iron oxide, ferrite, chromium oxide, Ni, an amorphous magnetic material, or permalloy. It is preferable to use, among these materials, one whose relative permeability $\mu s$ ($\mu/\mu 0$) is larger than or equal to 50 where $\mu$ is its permeability and $\mu 0$ is the permeability of the vacuum, even preferable to use one whose relative permeability $\mu s$ is 100 to 5,000, and most preferable to use one whose relative permeability $\mu s$ is 100 to 500. The ring-shaped member 70 whose relative permeability $\mu s$ is smaller than 50 is not preferable because in this range the above-described effect of concentrating the magnetic flux is weak. And, the ring-shaped member 70 whose relative permeability $\mu s$ is larger than 5,000 is not preferable because the magnetic flux narrowing effect is saturated in this range.

As shown in FIG. 9A, the power supply coil 55 which is composed of the ring-shaped member 70 and the cylindrical coil 60 is housed in a cylindrical coil case 80. The coil case 80 is configured such that, when its end surface (base surface) in the axial direction is seen from outside, a marker 3 (see FIG. 1) provided on a human body surface (skin surface) 2 can be seen through the inside of the cylindrical coil 60.

The coil case 80 which is approximately cylindrical is disposed so that its axis coincides with the axis of the cylindrical coil 60 and the ring-shaped member 70, that is, the coil case 80 is coaxial with the cylindrical coil 60 and the ring-shaped member 70. The coil case 80 houses the power supply coil 55 so as to cover the outside surface (in the radial direction) of the ring-shaped member 70 and the inside surface (in the radial direction) of the cylindrical coil 60. The coil case 80 is formed with a cylindrical penetration space 81 whose axis coincides with the axis of the cylindrical coil 60, whereby the marker 3 provided on the human body surface 2 can be seen through the penetration space 81 from the side of the base surface of the coil case 80 (see FIG. 9A).

A rounded outer edge portion 83 projects in the radial direction from the outer circumference of the tip, to come into contact with the body surface 2, of the coil case 80. With this measure, the power supply coil 55 can be set stably on the patient body surface 2 when it is brought into contact with the body surface 2.

The coil case 80 may be closed at least at one of its two ends in the axial direction. In the embodiment, a transparent member 85 is attached to the tip-side inner circumference of the coil case 80 so as to close the tip-side opening of the penetration space 81. The marker 3 on the body surface 2 can be seen through the transparent member 85 from the side of the base surface of the coil case 80 (see FIG. 9A). Alternatively, the transparent member 85 may be attached to the coil case 80 so as to close its base-side opening.

The transparent member 85 is provided with a marker 86 for positioning with respect to the marker 3 on the body surface 2, at the center, that is, on the axis of the cylindrical coil 60. Although in the embodiment the marker 86 is shaped like a circle (see FIG. 9B), it may be a cross mark or the like; there are no particular limitations on the shape of the marker 86.

Still further, as shown in FIG. 9A, the coil case 80 is formed with a lead-out hole 80a which communicates with the outside, on the base side in the axial direction. End portions of the lead wire 61 of the cylindrical coil 60 are put out of the coil case 80 through the lead-out hole 80a and connected to a power source 88 via an inverter circuit 87 (see FIG. 2). A DC current supplied from the power source 88 is converted by the inverter circuit 87 into an AC current having a prescribed voltage and frequency, which is supplied to the cylindrical coil 60.

It is preferable that the outer diameter of the coil case 80 (its cylindrical portion excluding the outer edge portion 83) be 25 to 65 mm, and it is even preferable that the outer diameter of the coil case 80 be 30 to 50 mm. It is preferable that the inner diameter of the coil case 80 be 20 to 60 mm (and equal to the outer diameter (20 to 60 mm) of the ring-shaped member 70), and it is even preferable that the inner diameter of the coil case 80 be 30 to 40 mm. It is preferable that the axial length of the coil case 80 be 10 to 50 mm, and it is even preferable that the axial length of the coil case 80 be 20 to 40 mm.

For example, the coil case 80 may be made of a transparent, insulative material such as silicone rubber, an epoxy resin, polycarbonate, or nylon.

Next, a description will be made of workings and advantages of the medical device 10 and power supply device 50 having the above configurations.

The device main body 15 which is part of the medical device 10 according to the embodiment is implanted into a human body and used as a pacemaker. As shown in FIG. 4, the lead wires 48 and 49 which are connected to the lead connection portion 27 of the device main body 15 are connected to an atrium and a ventricle of the heart 5 through a vein 7. When the device main body 15 is implanted, as shown in FIG. 1 a marker 3 is attached to the body surface 2 so that the position of the power reception coil 30 can be recognized.

As shown in FIG. 2, an electrocardiographic signal of the atrium and the ventricle of the heart 5 is input to the control circuit 46 via the lead wires 48 and 49 and the connectors 28 (sensing). The control circuit 46 judges whether or not the heart 5 is producing an irregular heartbeat or the like. If finding an irregular heartbeat or the like, the control circuit 46 sends an electrical signal to the lead wires 48 and 49 via the connectors 28. Thus, the atrium and the ventricle of the heart 5 are stimulated electrically (pacing), whereby the irregular heartbeat or the like of the heart 5 is corrected.

If the secondary battery 40 has become weak due to continued operation of the device main body 15, it is charged by the power supply device 50. To do this, as shown in FIG. 1, the axis of the coil case 80 of the power supply device 50 is registered with the marker 3 on the body surface 2 and the tip surface of the power supply device 50 is brought into contact with the body surface 2. In this state, the power supply coil 55 of the power supply device 50 is opposed to the power reception coil 30 of the device main body 15 with their axes approximately coincident with each other and with the body surface 2 interposed between them.

Since as shown in FIG. 9A the coil case 80 of the power supply device 50 is configured such that the marker 3 on the body surface 2 can be seen through the inside space of the cylindrical coil 60 when the coil case 80 is viewed from outside, that is, from the side of its base surface, the axis of the coil case 80 can easily be positioned with respect to the marker 3 on the body surface 2. Thus, the tip surface of the power supply device 50 can be brought into contact with a prescribed portion of the body surface 2 correctly and smoothly.

Since the transparent member 85 is provided at least at the tip (one end) of the coil case 80 and the coil case 80 is formed with the cylindrical penetration space 81 whose axis coincides with the axis of the cylindrical coil 60, the marker 3 provided on the human body surface 2 is high in visibility when the tip surface of the coil case 80 is viewed from outside. As a result, the accuracy of positioning of the coil case 80 with respect to the marker 3 can be made even higher.

Figure 10:
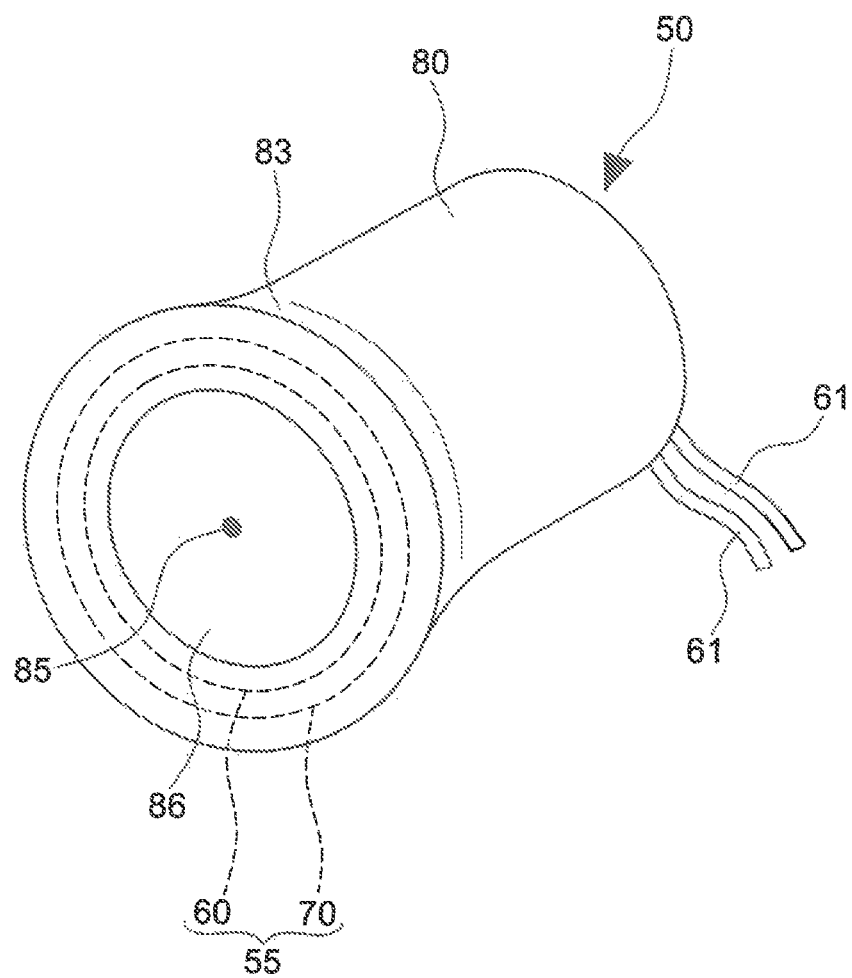
FIG. 10 is a perspective view of the power supply coil.

Since as shown in FIGS. 9A and 9B and FIG. 10 the marker 86 for positioning with respect to the marker 3 on the body surface 2 is provided at the center of the transparent member 85, the center of the transparent member 85 can be positioned accurately with respect to the marker 3 on the body surface 2.

As described above, the tip surface of the power supply device 50 is brought into contact with the body surface 2 with the axis of the coil case 80 of the power supply device 50 positioned with respect to the marker 3 on the body surface 2, whereby the power supply coil 55 of the power supply device 50 is opposed to the power reception coil 30 of the device main body 15 (see FIG. 1). The power source 88 for the power supply device 50 is thereafter turned on, whereupon an AC current produced through conversion by the inverter circuit 87 is supplied to the lead wires 61 of the cylindrical coil 60 of the power supply device 50.

As a result, a magnetic field is generated by the power supply coil 55 of the power supply device 50 and a resulting magnetic flux crosses the power reception coil 30 of the device main body 15 (see FIG. 1), whereby power is transferred to the power reception coil 30 through electromagnetic induction (wireless supply of power). A resulting AC current flowing through the power reception coil 30 is supplied to the rectifier/regulator circuit 44, which converts it into a prescribed DC voltage. The DC voltage is supplied to the charging circuit 45, which charges the secondary battery 40 (see FIG. 2).

In the power supply device 50 and the medical device 10, since the power supply coil 55 is configured such that the ring-shaped member 70 made of a magnetic material is disposed so as to surround the outer periphery of the cylindrical coil 60, the width W (see FIG. 11A) of the range where a magnetic flux that flows into or out of each end of the power supply coil 55 is concentrated.

Figure 11A:
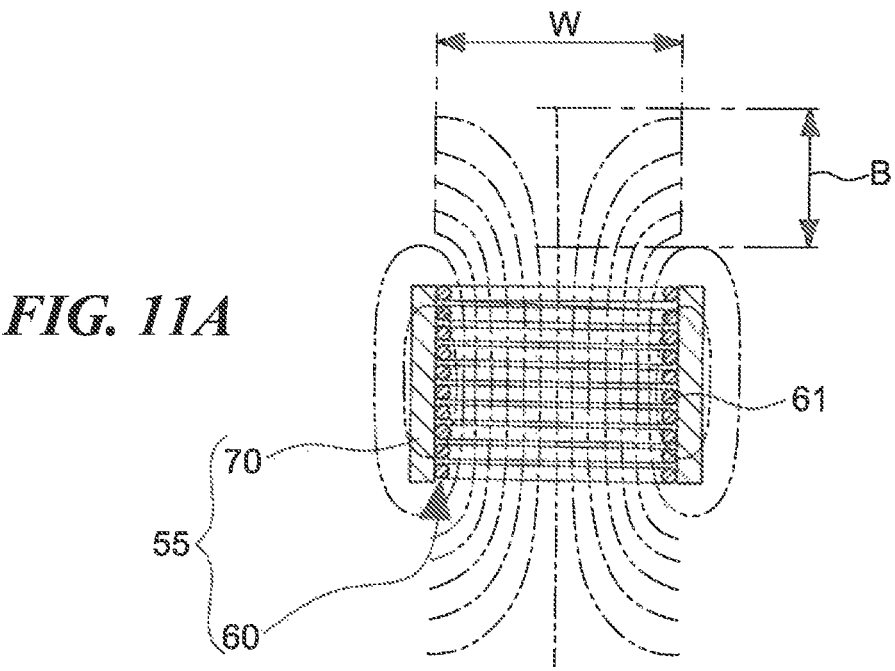
FIG. 11A illustrates how the power supply coil used in the embodiment works.
Figure 11B:
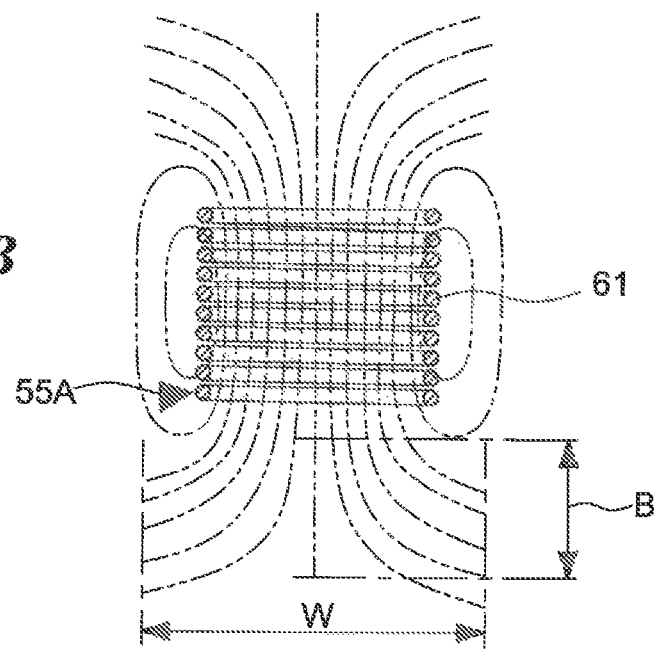
FIG. 11B illustrates how a conventional power supply coil works.

FIG. 11B shows a power supply coil 55A which does not have the ring-shaped member 70 outside the cylindrical coil 60 which is wound helically, while the power supply coil 55 has the ring-shaped member 70 disposed so as to surround the outer periphery of the cylindrical coil 60 as shown in FIG. 11A.

A magnet flux produced by the power supply coil 55 is caused to be dense at a radial range between the coil axis to the coil diameter portion, and is caused to be crude at a radial range outside the coil diameter portion. Assuming an axial region B apart from the end surface of the power supply coil 55 (the end surface of the cylindrical coil 60 and the end surface of the ring-shaped member 70 are made to coincide) as illustrated in FIGS. 11A and 11B, the width W of the range where the magnetic flux produced by the power supply coil 55 is concentrated can be narrowed than that of the power supply coil 55A. The axial region B may extend from the axial position 10 mm away from the end surface of the power supply coil 55 to the axial position 30 mm away from the end surface of the power supply coil 55. Thus, the power supply coil 55 will be applicable regardless of, for example, whether the patient's body is thin or thick and whether the patient is child or adult.

This is considered due to a phenomenon that since the ring-shaped member 70 is disposed outside the cylindrical coil 60, a magnetic flux produced by the cylindrical coil 60 tends to be guided to and permeate through the ring-shaped member 70 which is made of a magnetic material and hence is high in relative permeability μs and expansion of the magnetic flux is thereby suppressed.

In the power supply device 50 and the medical device 10, since the power supply coil 55 is configured such that the ring-shaped member 70 made of a magnetic material is disposed so as to surround the outer periphery of the cylindrical coil 60 and hence the width W of the range where a magnetic flux produced by the power supply coil 55 is concentrated can be narrowed, the components other than the power reception coil 30 of the device main body 15 implanted in a human body, such as the various circuit components 43 of the driving device 41 and the lead wires 48 and 49 can be made not prone to be affected by magnetism.

The medical device 10 is equipped with the power reception coil 30 and power is supplied from outside the human body, that is, from the power supply device 50, using the power reception coil 30. Unlike in the electronic device for use in a living body disclosed in JP-3743152-B which has, inside, the mechanical power generation structure including the large and small gears, in the medical device 10 the secondary battery 40 can be charged without using such a mechanical structure. Thus, the medical device 10 can be made compact and enables reduction of the burden of a patient.

In the medical device 10 according to the embodiment, the secondary battery 40 and the driving device 41 of the device main body 15 are housed in the shield case 25 which interrupts magnetism and the power reception coil 30 is disposed outside the shield case 25 and integrated with the device main body 15 such that the insulator 35 is interposed between the coil member 33 and the shield case 25.

With this configuration, when wireless supply of power is performed from the power supply device 50 via the power reception coil 30, a magnetic flux produced by the power supply coil 55 is attracted by and permeates through the walls of the shield case 25. Referring to FIG. 1, of a magnetic flux that goes from the power supply coil 55 toward the secondary battery 40 or the driving device 41 (i.e., a magnetic flux around the left-hand part of the power supply coil 55), a magnetic flux B1 that is distant from the axis of the power supply coil 55 is attracted by and permeates through a wall 25a, located on the side of the body surface 2, of the shield case 25 and a magnetic flux B2 near the axis of the power supply coil 55 is attracted by and permeates through a wall 25b, distant from the body surface 2, of the shield case 25.

Since as described above the magnetic flux produced by the power supply coil 55 is attracted by and permeates through the walls of the shield case 25, influence of magnetism on the secondary battery 40, the various circuit components 43 of the driving device 41, etc. can be suppressed.

Since the power reception coil 30 is disposed outside the shield case 25 and integrated with the device main body 15 such that a part of the insulator 35 is interposed between the coil member 33 and the shield case 25, the medical device 10 can be made compact. Thus, the medical device 10 can be implanted into a human body relatively easily.

In the medical device 10 according to the embodiment, the device main body 15 is equipped with the main body case 20 made of Ti or a Ti alloy and the shield case 25 which is disposed inside the main body case 20. The power reception coil 30 is not housed in the shield case 25 but housed in the main body case 20. With this configuration, since the power reception coil 30 is housed in the main body case 20 which is made of Ti or a Ti alloy and hence is highly biocompatible, the implant medical device 10 can be made compact, easy to handle, and efficient in implanting work.

An implant medical device 10A according to another embodiment of the invention will be described below with reference to FIG. 12.

The implant medical device 10A (hereinafter referred to simply as a "medical device 10A") according to this embodiment is different from the medical device 10 according to the above embodiment in the structure of a main body case 20A.

More specifically, the wall of the main body case 20A used in this embodiment has a double-layer structure consisting of an outer layer 23a and an inner layer 23b which is disposed inside the outer layer 23a. The outer layer 23a is made of Ti or a Ti alloy. On the other hand, the inner layer 23b may be made of a metal that is lower in electrical resistivity than Ti, such as Cu, Al, Ni, Fe, or Zn, or an alloy thereof. As a result, the main body case 20A can prevent entrance of magnetism to the inside of the main body case 20A. Among Fe alloys, stainless steel is not preferable because it is higher in electrical resistivity than Ti. Alternatively, the inner surface of the outer layer 23a may be plated with any of the above-mentioned metals such as Cu, Al, Ni, Fe, and Zn.

Figure 12:
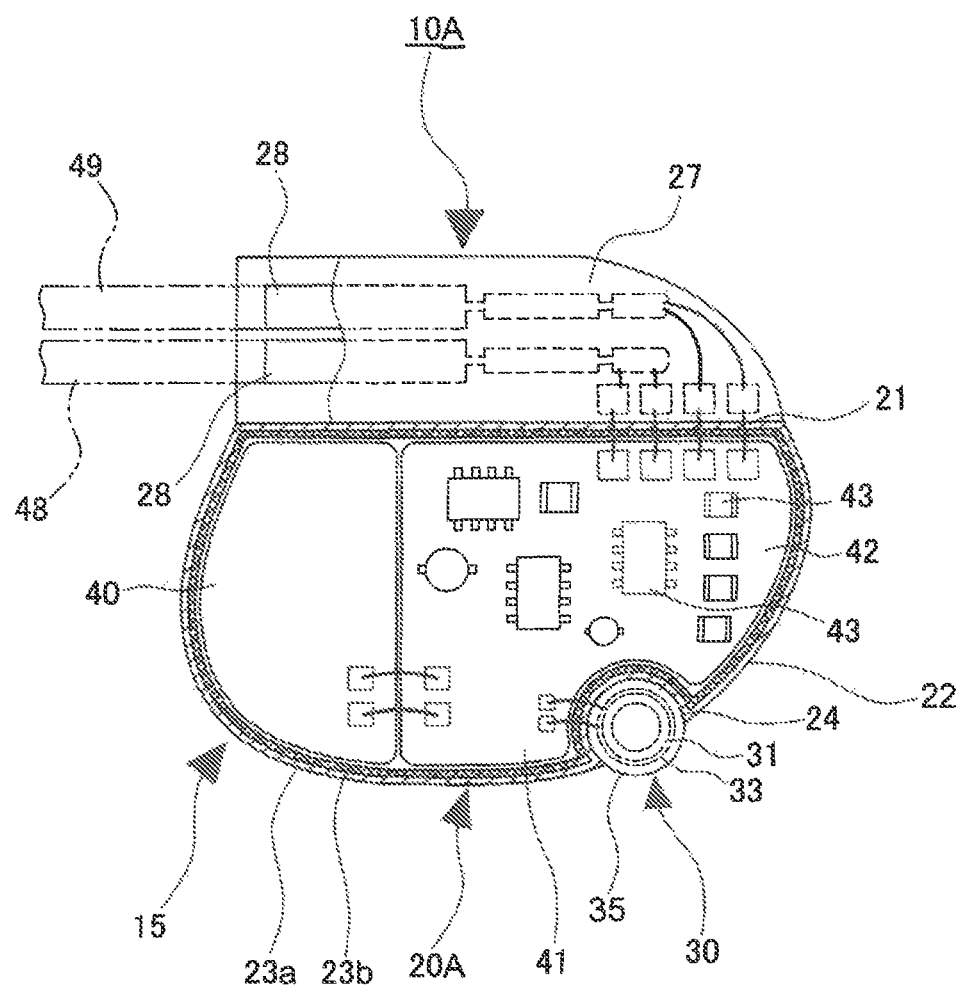
FIG. 12 is a partially sectional view of an implant medical device according to another embodiment.

As shown in FIG. 12, the circumferential wall 22 of the main body case 20A is formed with an approximately circular-arc-shaped recess 24 at such a position that it is opposed to the partition wall 21. The recess 24 is fitted with the insulator 35 of the power reception coil 30 so that the power reception coil 30 is disposed outside and integrated with the main body case 20A with part of the insulator 35 interposed between the coil member 33 and the main body case 20A. The position, shape, etc. of the recess 24 shown in FIG. 12 are just examples, and there are no particular limitations on them. However, it is preferable that the recess 24 be as distant from the lead wires 48 and 49 (which are connected to the connectors 28) as possible.

The invention is not limited to the above embodiments. Various modifications are possible without departing from the spirit and scope of the invention, and such modifications will also fall under the scope of the invention.

[Example]

A power supply device 50 and an implant medical device 10 having the same configurations as shown in FIGS. 1 and 3 were manufactured.

(Manufacture of Implant Medical Device 10)

A core body 31 of a power reception coil 30 was made of ferrite and had an outer diameter 7 mm, a thickness 0.2 mm, and an axial length 5 mm. A coil member 33 having an outer diameter 7.16 mm (inner diameter 7 mm) and an axial length 5 mm was formed by winding a lead wire 32 of 0.08 mm in diameter in 100 turns and two layers. An insulator 35 was made of a silicone resin and had an outer diameter 10 mm and an axial length 6 mm.

A shield case 25 and a main body case 20 of a device main body 15 were made of ferrite and Ti, respectively. A secondary battery 40 was an all-solid-state secondary battery that was 150 mA·h in capacity and generated a voltage 3.2 V.

(Manufacture of Power Supply Device 50 (Example))

A cylindrical coil 60 (of a power supply coil 55) having an outer diameter 30 mm and an axial length 30 mm was formed by winding a lead wire 61 of 0.8 mm in diameter helically so that a gap of 0.2 mm was formed between adjoining turns. A ring-shaped member 70 to be disposed outside the cylindrical coil 60 was made of Fe having relative permeability is 5,000 and had an outer diameter 48 mm, a thickness 2.5 mm, and an axial length 30 mm. A coil case 80 was made of polycarbonate and had an outer diameter 50 mm and an axial length 40 mm.

(Manufacture of Power Supply Device (Comparative Example))

A power supply device of Comparative Example was manufactured that was the same as the power supply device 50 of Example except that the former was not equipped with the ring member 70; that is, a power supply device having a power supply coil 55A shown in FIG. 11B was manufactured.

(Experiment for Comparison Between Magnetic Flux Densities)

An AC current of 1 A was caused to flow through each of the power supply coil 55 of the power supply device 50 of Example and the power supply coil 55A of the power supply device of Comparative Example, and a variation of the magnetic flux density with respect to the distance in the radial direction from the coil axis at the axial position 15 mm away from the end surface of the power supply coil 55 (the end surface of the cylindrical coil 60 and the end surface of the ring-shaped member 70 are made to coincide) was measured. Results are shown in FIG. 13.

Figure 13:
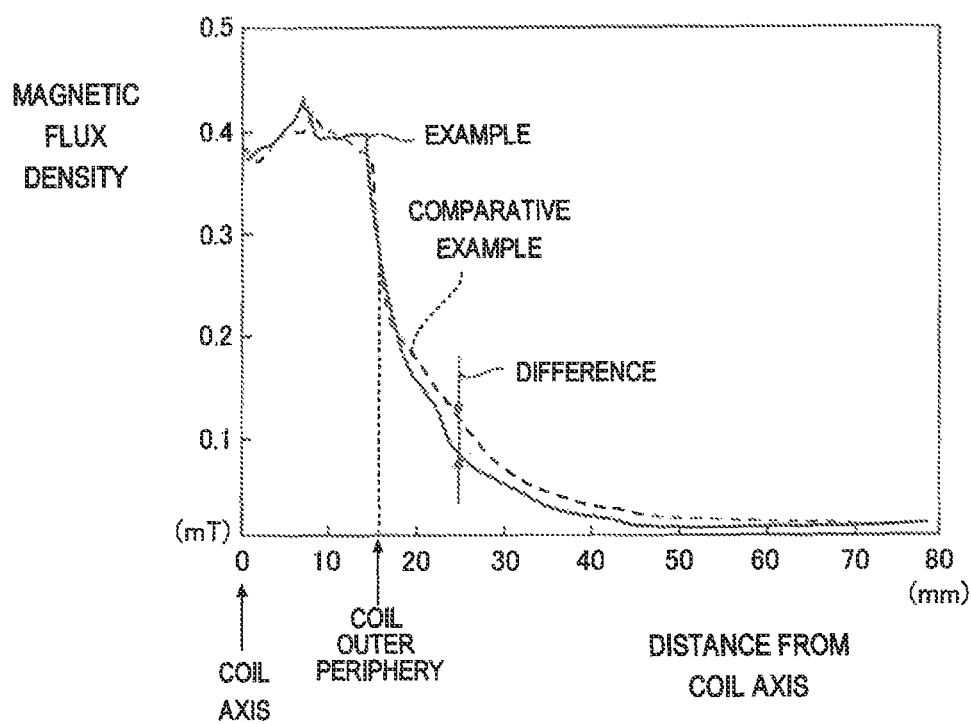
FIG. 13 is a graph showing relationships between the distance from the coil axis and the magnetic flux density in cases that an AC current was caused to flow through a power supply coil of Example and a power supply coil of Comparative Example.

As seen from FIG. 13, the power supply device 50 of Example and the power supply device of Comparative Example exhibited approximately the same magnetic flux density values from the coil axis (15 mm) to a position (about 18 mm) a little outside the outer periphery of the coil and had approximately the same magnetic flux density curves in this range. However, from around the position (about 18 mm) a little outside the outer periphery of the coil, they came to exhibit different magnetic flux density values, that is, the magnetic flux density of the power supply device 50 of Example having the ring-shaped member 70 became smaller than that of the power supply device of Comparative Example not having the ring-shaped member 70. This result shows that the magnetic flux generated by the power supply device 50 of Example is more concentrated than the magnetic flux generated by the power supply device of Comparative Example. This verifies that with the power supply device 50 of Example the circuit components 43 of the driving device 41 and other components of the device main body 15 are not prone to be affected by magnetism.

It has been confirmed that the power supply device 50 of Example can charge the secondary battery 40 of the device main body 15 properly. For example, an all-solid-state secondary battery that is 150 mA·h in capacity and generates a voltage 3.2 V like the secondary battery 40 of Example can be charged up in about 45 min when charged under the conditions of 0.4 W and 200 mA.

The invention claimed is:

1. A power supply device for supplying power to a medical device main body implanted in a human body, the power supply device including:
    a power supply coil configured to supply power wirelessly to a power reception coil provided in the medical device main body from outside the human body through electromagnetic induction,
    wherein the power supply coil includes:
        a cylindrical coil formed by winding a lead wire helically;
        a ring-shaped member made of a magnetic material and disposed so as to surround an outer circumference of the cylindrical coil; and
        a cylindrical coil case housing the ring-shaped member surrounding a cylindrical coil,
    wherein the cylindrical coil case houses the power supply coil so as to cover an outside surface in a radial direction of the ring-shaped member and an inside surface in the radial direction of the cylindrical coil,
    wherein the coil case is configured to make a marker provided on a human body surface visible through an inside space of the cylindrical coil when an end surface of the coil case in an axial direction thereof is viewed from outside,
    wherein at least one of end walls of the coil case comprises a transparent member, and/or
    wherein coil case has a penetration space which is defined along an axis of the cylindrical coil.

2. The power supply device of claim 1, wherein a diameter of the lead wire is in a range from 0.1 mm to 1.0 mm.

3. The power supply device of claim 2, wherein the diameter of the lead wire is in a range of 0.2 mm to 0.5 mm.

4. The power supply device of claim 1, wherein the outer diameter of the cylindrical coil is in a range of 10 mm to 50 mm.

5. The power supply device of claim 4, wherein an outer diameter of the cylindrical coil is in a range of 20 mm to 30 mm.

6. The power supply device of claim 1, wherein an axial length of the cylindrical coil is in a range of 10 mm to 50 mm.

7. The power supply device of claim 1, wherein an axial length of the cylindrical coil is in a range of 20 mm to 30 mm.

8. The power supply device of claim 1, wherein the ring-shaped member surrounds the outer circumference of the cylindrical coil such that a tip of the cylindrical coil and a tip of the ring-shaped member are at a same location in an axial direction.

9. The power supply device of claim 1, wherein the cylindrical coil case includes a rounded outer edge portion that projects in a radial direction from an outer circumference of a tip of the cylindrical coil case.

10. The power supply device of claim 1, wherein the cylindrical coil case is closed at least at one of its two ends in an axial direction.

11. The power supply device of claim 1, wherein the transparent member is provided with a marker to make a second marker provided on a human body surface visible through an inside space of the cylindrical coil when an end surface of the coil case in an axial direction thereof is viewed from outside.

12. An implant medical device including:
    a medical device main body to be implanted into a human body; and
    a power supply device for supplying power to the medical device main body from outside the human body,
    wherein the medical device main body includes:
        a power reception coil;
        a secondary battery configured to store power generated by the power reception coil; and
        a driving device driven by the secondary battery,
    wherein the power supply device includes:
        a power supply coil configured to supply power to the power reception coil wirelessly through electromagnetic induction, and
    wherein the power supply coil includes:
        a cylindrical coil formed by winding a lead wire helically;
        a ring-shaped member made of a magnetic material and disposed so as to surround an outer circumference of the cylindrical coil; and
        a cylindrical coil case housing the ring-shaped member surrounding the cylindrical coil, and
    wherein the cylindrical coil case houses the power supply coil so as to cover an outside surface in a radial direction of the ring-shaped member and an inside surface in a radial direction of the cylindrical coil.

13. The implant medical device of claim 12,
    wherein the secondary battery and the driving device are housed in a shield case formed to interrupt magnetism, and
    wherein the power reception coil is disposed outside the shield case, and is integrated with the medical device main body with an insulator interposed between the power reception coil and the shield case.

14. The implant medical device of claim 13,
    wherein the medical device main body includes:
        a main body case made of Ti or a Ti alloy and formed to house the shield case, and
    wherein the power reception coil is not housed in the shield case but housed in the main body case.

15. A power supply device for supplying power to a medical device main body implanted in a human body, the power supply device including:
    a power supply coil configured to supply power wirelessly to a power reception coil provided in the medical device main body from outside the human body through electromagnetic induction,
    wherein the power supply coil includes:
        a cylindrical coil formed by winding a lead wire helically;

a ring-shaped member made of a magnetic material and disposed so as to surround an outer circumference of the cylindrical coil; and a cylindrical coil case housing the ring-shaped member surrounding a cylindrical coil, wherein the cylindrical coil case houses the power supply coil so as to cover an outside surface in a radial direction of the ring-shaped member and an inside surface in the radial direction of the cylindrical coil, and wherein the cylindrical coil case is disposed so an axis of the cylindrical coil case coincides with an axis of both of the cylindrical coil and the ring-shaped member.

\* \* \* \* \*